United States Patent [19]
Coughlin et al.

[11] Patent Number: 6,107,085
[45] Date of Patent: Aug. 22, 2000

[54] SELF CONTAINED CELL GROWTH SYSTEM

[75] Inventors: Paul Thomas Coughlin, Kennebunk; George Frederick Lyman, Kennebunk Port, both of Me.; Gregory Mathus, Corcord, Mass.

[73] Assignee: Corning Incorporated, Corning, N.Y.

[21] Appl. No.: 09/110,754

[22] Filed: Jul. 3, 1998

Related U.S. Application Data

[60] Provisional application No. 60/052,311, Jul. 11, 1997.

[51] Int. Cl.[7] .................................................... C12M 3/04
[52] U.S. Cl. .................................. 435/299.1; 435/299.2; 435/304.2; 435/289.1
[58] Field of Search ............................. 435/293.1, 295.1, 435/299.1, 299.2, 304.1, 304.2, 284.1, 395, 399, 401, 289.1; 210/615, 150; 623/15

[56] References Cited

U.S. PATENT DOCUMENTS

| | | | |
|---|---|---|---|
| 3,853,712 | 12/1974 | House et al. | 195/127 |
| 4,225,671 | 9/1980 | Puchinger et al. | 435/71 |
| 4,228,243 | 10/1980 | Iizuka et al. | 435/285 |
| 4,668,632 | 5/1987 | Young et al. | 435/284 |
| 4,683,062 | 7/1987 | Krovak et al. | 210/617 |
| 4,734,373 | 3/1988 | Bartal | 435/296 |
| 4,774,187 | 9/1988 | Lehmann | 435/313 |
| 5,100,801 | 3/1992 | Ward, Jr. et al. | 435/296 |
| 5,240,854 | 8/1993 | Berry et al. | 435/284 |
| 5,262,320 | 11/1993 | Stephanopoulos et al. | 435/240 |
| 5,316,945 | 5/1994 | Minuth | 435/285 |
| 5,376,548 | 12/1994 | Matsuo et al. | 435/284 |
| 5,466,602 | 11/1995 | Lyman et al. | 435/297.1 |
| 5,585,266 | 12/1996 | Plitt et al. | 435/240.23 |
| 5,658,797 | 8/1997 | Bader | 435/284.1 |
| 5,763,267 | 6/1998 | Kurjan et al. | 435/293.1 |
| 5,766,949 | 6/1998 | Liau et al. | 435/395 |

FOREIGN PATENT DOCUMENTS 89-011779/02  5/1987  Japan .

*Primary Examiner*—William H. Beisner
*Attorney, Agent, or Firm*—Thomas R. Beall

[57] ABSTRACT

The present application relates generally to a system for the practice of high density cell culture. The system employs the use of two tanks; a cell growth tank having multiple cell growth chambers, is preferably situated within a reservoir tank. A series of pumps and outlets provide an even and continuous circulation of media and air to the system and between tanks. The system is designed to operate with minimal supervision and constantly over long periods of time.

12 Claims, 12 Drawing Sheets

SELF CONTAINED CELL GROWTH SYSTEM

This application claims the benefit of the priority filing date of U.S. Provisional Application No. 60/052,311, filed Jul. 11, 1997.

FIELD OF THE INVENTION

The invention relates to a product for the culture of cells.

BACKGROUND OF THE INVENTION

Conventionally, cells have been grown attached to glass or plastic roller bottles and flasks. This approach does not lend itself to high density growth of cells or continuous cell culture, and requires large amounts of medium and space. Further, the approach is labor intensive.

To achieve higher density growth conditions, various attempts have been made to use arrangements of stacked plates, the surfaces of the stacked plates providing increased surface area for cell attachment and growth. In spite of various attempts, the cell culturing devices of the prior art all have various drawbacks, including the need for excessive amounts of medium, the inability to provide a continuous flow of nutrients to all cell-growth surfaces, the need for labor intensive monitoring and care of the growing cells and the inability to operate continuously.

One attempt to solve the problems of the prior art is disclosed in commonly assigned U.S. Pat. 5,240,854. This patent discloses a cell culture system for large scale production of cells and cell products. While this culture system solves many of the problems of the prior art, a demand exists for a similar device for small scale production. The advantage of having a cell culture system of small scale, such as the present invention, is twofold. First, the cost of a smaller system would enable smaller scale facilities to harvest cells with minimal effort and thereby save the expense of purchasing a larger scale unit. Second, a smaller unit would enable users to test and perfect procedures and growth conditions for a particular application, in the laboratory, and prior to transferring to a large scale production level system.

SUMMARY OF THE INVENTION

It is therefore an objective of the present invention to provide a cell culture device having the following characteristics: high cell growth density compared to the amount of nutrient medium in the system; an even flow of medium over a plurality of growth chambers; automatic and continuous addition of nutrient medium and removal of medium containing waste; a self contained media oxygenator; a self contained media reservoir; a pre-plumbed system having a minimum of sterile connections; a continuously monitored cellular environment; the ability to harvest cell products such as biochemicals, vaccine virus, and pharmaceuticals; cost effectiveness; and usefulness for small scale experimental pilot projects.

DETAILED DESCRIPTION OF THE PREFERRED EMBODIMENTS

The cell culture device of the preferred embodiment includes two separate tanks, one smaller cell growth tank seated within a larger reservoir tank holding cell growth media. Ideally, the media will circulate from the reservoir tank through the cell growth tank, and back to the reservoir tank.

Figure 1:
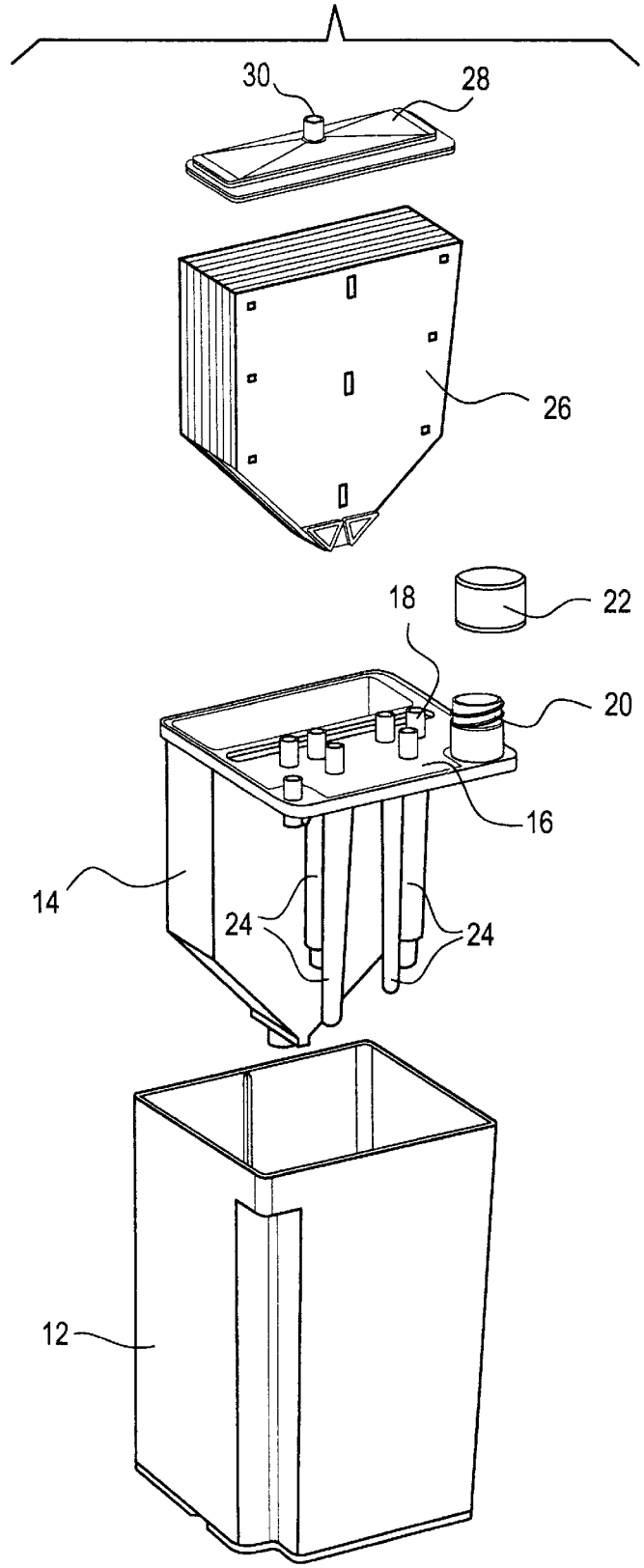
FIG. 1 is an exploded view of the cell growth system of the present invention.

FIG. 1 shows an exploded view of the preferred embodiment of the present invention. The reservoir tank 12 is a substantially rectangular box having roughly a square horizontal cross-section. The inner cell growth tank 14 and attached reservoir tank lid 16 fixably insert within the reservoir tank 12. The reservoir tank lid 16 has projecting from it, a series of nozzles or fittings 18 capable of attachment to hoses, and a container neck 20 capable of receiving a screw-on cap 22. Below the lid, and in fluid communication with certain nozzles, are a series of tubes 24 that descend downward into the reservoir tank 12. As will be discussed later, the tubes descend to varying depths within the reservoir tank. A cartridge of stacked plates 26 fixably mounted together, fits slideably into the cell growth tank 14. The individual plates are preferably all shaped identically, and the cartridge as a whole preferably conforms roughly to the interior dimensions of the cell growth tank 14. A lid 28 having a penthouse roof shape covers the cell growth tank 14. The lid 28 has an outlet conduit 30 in the form of a nozzle located at its peak. The nozzle is capable of attachment to a hose.

Figure 2:
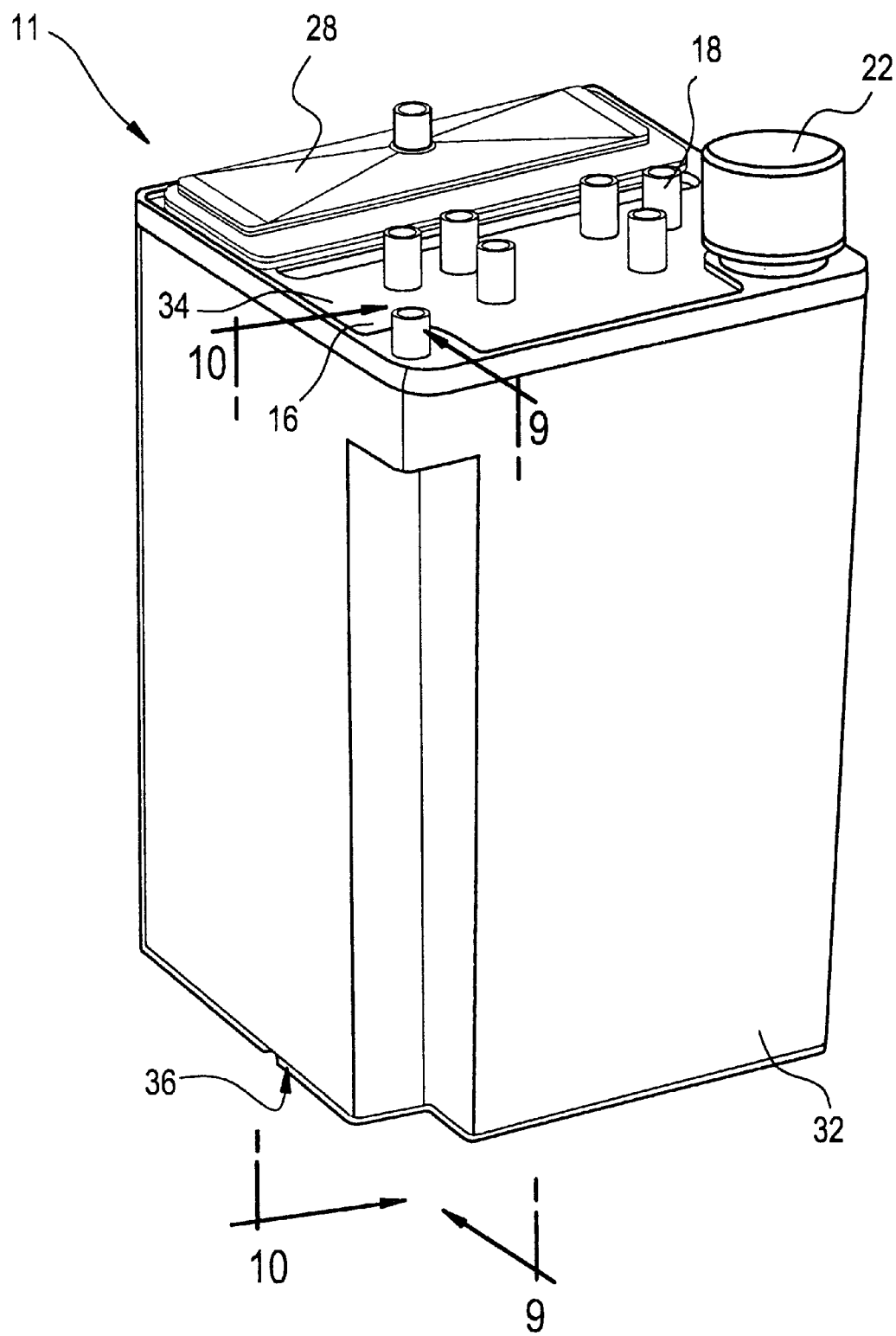
FIG. 2 is a three dimensional view of the cell growth system of the present invention.

Once assembled, as shown in FIG. 2, the cell culture device 11 appears as a unit having four vertical side walls 32, a top surface 34, and a bottom 36. The top surface comprises the lid 16 covering the reservoir tank and the lid 28 covering the cell growth tank. From the top surface, a plurality of air and liquid tight fittings 18 protrude upwardly. A screw-on cap 22, covers a neck providing access to the reservoir tank. As an alternative to a standard cap, a vent cap, with integral sterility filter can be used to help vent the system.

Figure 3A:
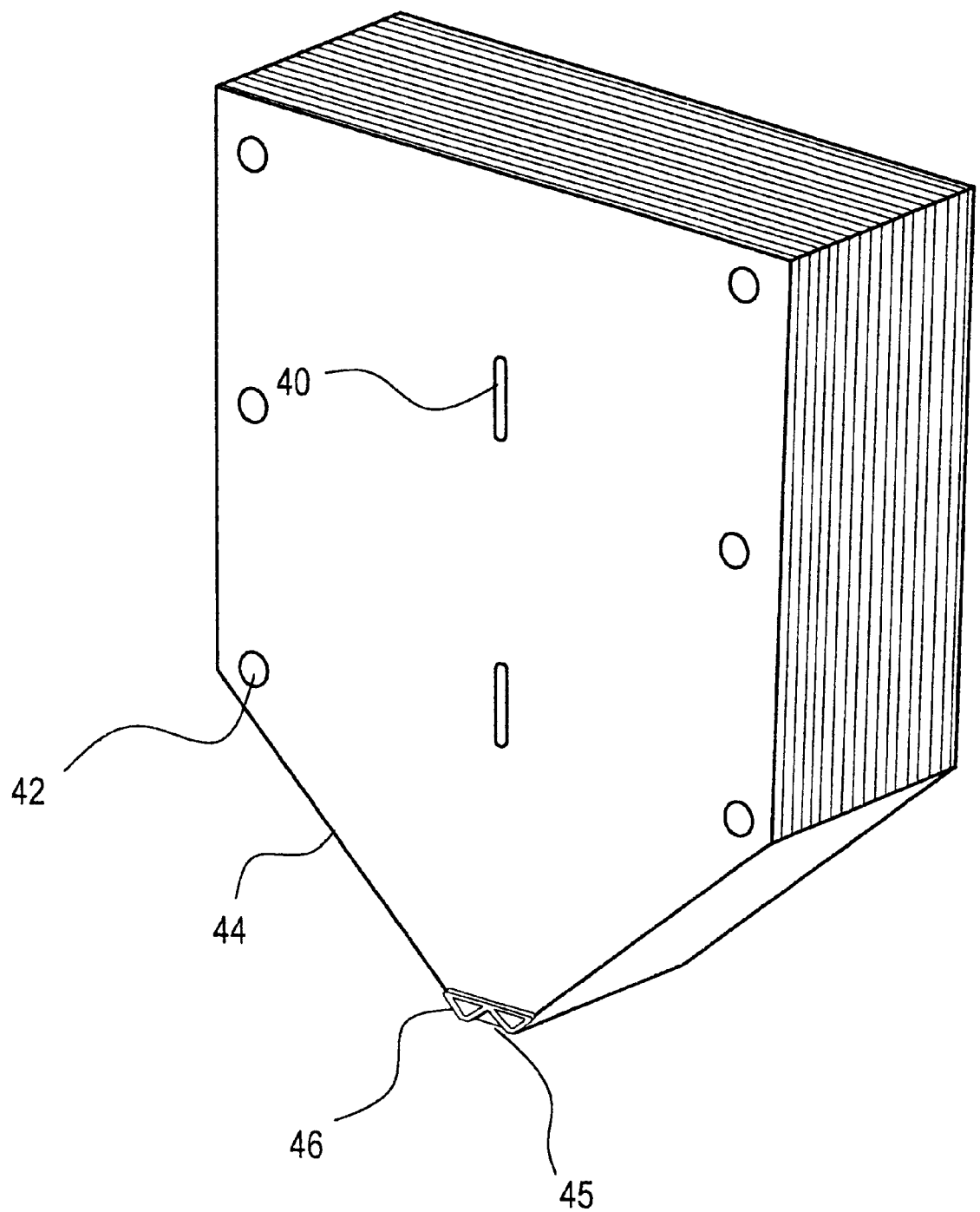
FIG. 3A is a three dimensional view of a cartridge of stacked plates that, together with the cell growth tank, form the cell growth chambers of the present invention.

FIG. 3A shows a plurality or cartridge 26 of plates that, together with the side walls of the growth tank, form the growth surface for cells. The space between each stacked plate defines individual growth chambers. Cell growth may occur on the plates forming both sides of this chamber. Preferably, 15 plates are spaced 0.04 inches apart or greater.

Of course, the system is scaleable and the number of plates may be increased or decreased accordingly. Although the plates may be spaced closer to one another, air bubbles tend to become trapped between the plates and interrupt the even flow of medium when spaced less than about 0.04 inches apart. The surfaces of the plates may be roughened, corrugated, convoluted or otherwise irregular to increase their surface area and the number of cells capable of growing on a given plate. If irregular, the 0.04 inch spacing between the plates should be between the facing peaks of irregular surfaces. The surfaces of plates may also be surface treated in a variety of different ways in order to promote cell growth. Typical treatments include carboxyl group treatments, collagen treatments, plasma treatments, fibronectin treatments, or feeder cell layers.

The plates according to the preferred embodiment are molded from polystyrene. Suitable plate materials include styrenic materials, polyester, polycarbonate, polymethyl pentene or K-resin. However, the plate may be made of virtually any material that is sufficiently strong, nontoxic, biocompatible, and otherwise suitable for cell tissue culture.

The plates of the present invention have a construction that facilitates flow distribution and manufacturing. Preferably, each of the plates are designed with at least one 0.04 inch high rib 40 or bead on their surface. The six raised pins 42 on the sides of the plate are also preferably 0.04 inches high, so that when the plates are stacked, the open area between plates is uniformly 0.04 inches thick. The pins 42 interlock with corresponding pins of successive plates and thereby serve to hold the stack of plates together while also preventing warpage of individual plates.

Plates can be made without the centralized rib portion for instances in which a confluent layer of cells is desired for harvest, for skin transplants, as an example. In these instances, the pins may serve as the only means for maintaining the required separation between plates.

Figure 3B:
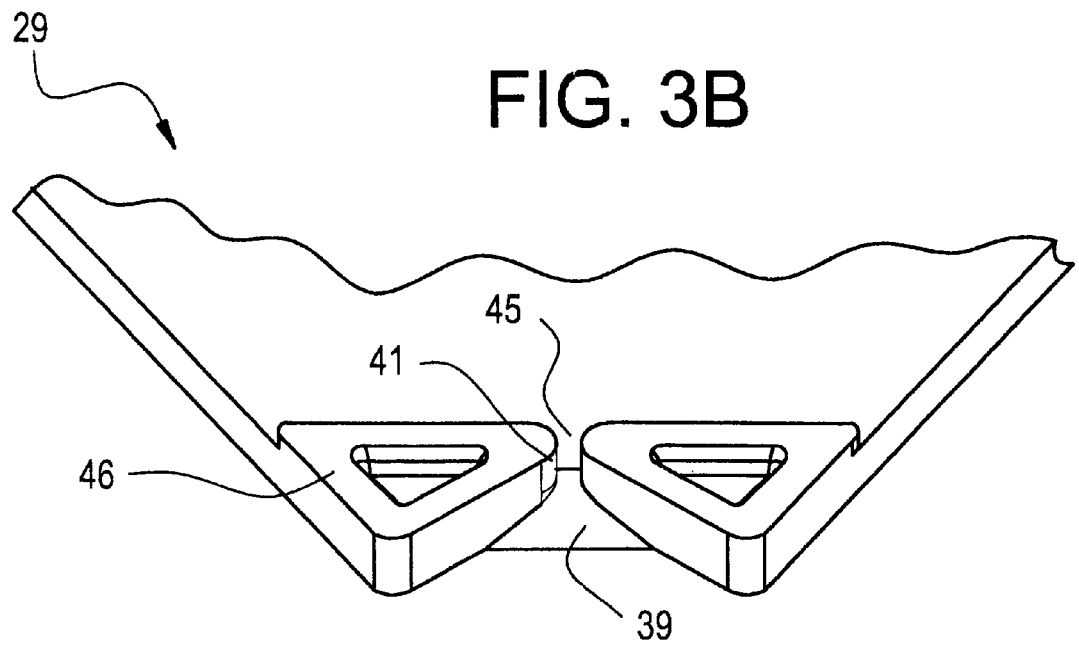
FIG. 3B is a three dimensional expanded view of a portion of a plate of the present invention.
Figure 3C:
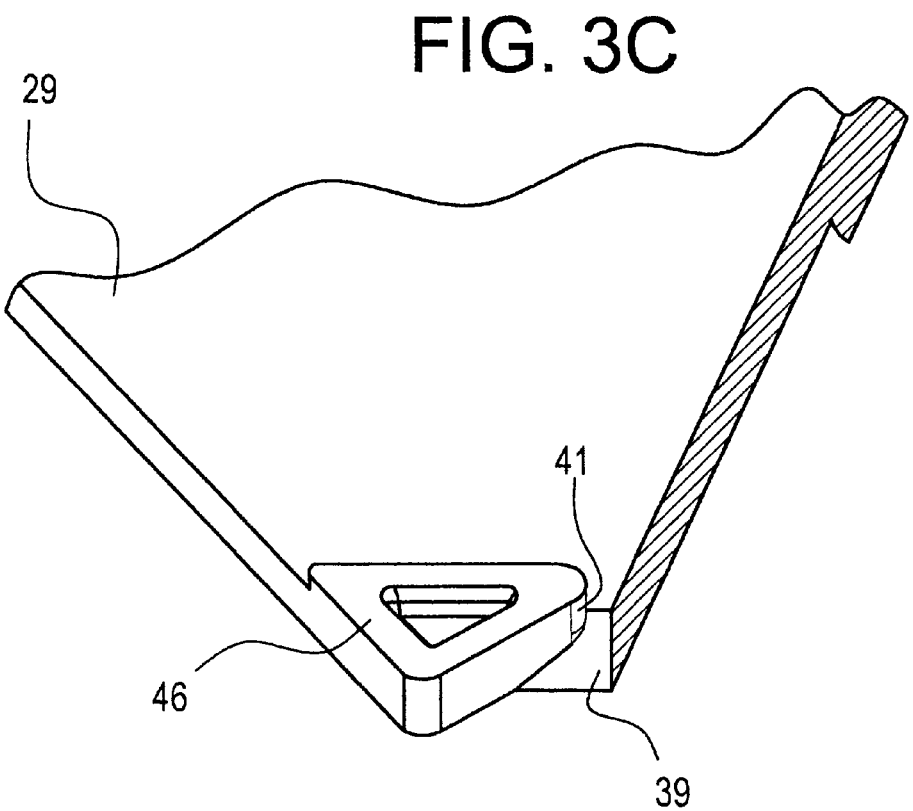
FIG. 3C is a bisection of FIG. 3B.

Further, the plates are preferably rectangular in shape with a tapered section 44 narrowing to a double triangle point 46. As shown in FIG. 3B, a three dimensional partial view of a plate 29, each triangle is molded onto one side of a plate surface and raised 0.04 inches above the plate surface. A passage 45 extends between the triangle shaped features to the interior space defined by the side walls of the stacked plates. Each passage has side walls defined by chamfered corners 41 of the two raised triangular features 46, the plate surface, and the flat under surface of an opposing stacked plate. The extreme end of the plate is a beveled edge 39 which serves to break up and reduce the size of any bubbles that may enter through the passage 45. FIG. 3C shows a section cut of the plate 29, bisecting the passage 45 of FIG. 3B. The beveled entry 39 to the chamber can be seen clearly. The particular shape of the passage in the preferred embodiment includes a narrowed internal portion having a width of 0.04 inches. The cross-section of the passage then increases continuously and in a direction toward the growth chamber. The passage may be shaped in any of a variety of ways, including straight walled, walls flaring in, walls flaring out, or walls narrowed in the center, for example.

Figure 3D:
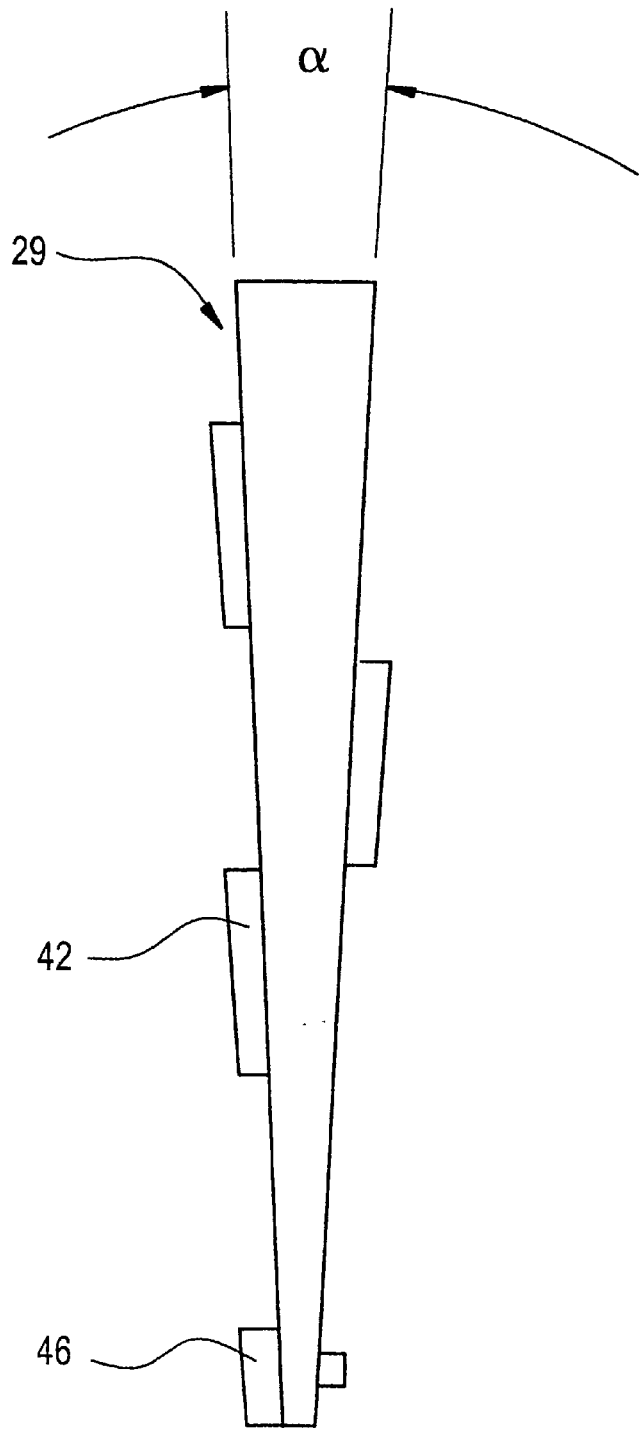
FIG. 3D is a cross-section of a plate of the present invention.

It is preferred that the plates fit into the growth tank such that, taken as a whole, they roughly conform to the shape of the tank. For this reason, it is preferred that the plates increase in thickness from one end to the other as shown in the exaggerated plate cross section of FIG. 3D. Pins 42 are shown on both sides of the plate 29. These pins will interlock with pins from successive plates. The pins 42 and the triangular element 46 are all raised 0.04 inches above the surface of the plate. This way, the chambers that are formed by the plates will remain a uniform 0.04 inches in width, while the plates, taken as a whole will conform to the slight draft angle of the side walls on the cell growth tank. Maintaining a uniform chamber width facilitates a smooth and even flow of media through the cell growth tank. The edges of the plates are also preferably molded with a draft that conforms with the draft on the end walls of the growth tank.

Figure 4:
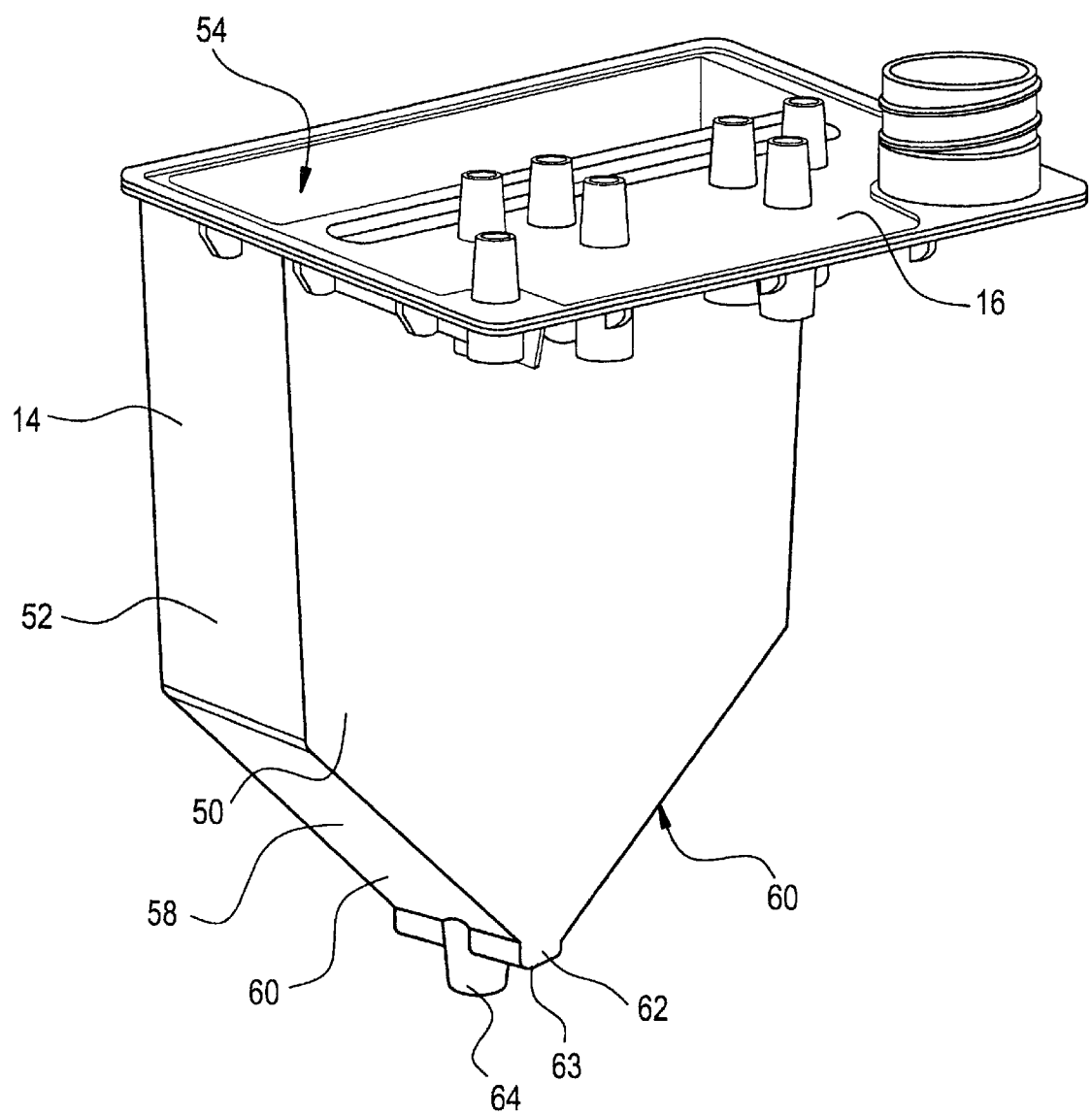
FIG. 4 is a three dimensional view of a one piece combination construction of a reservoir tank lid and cell growth tank of the present invention.

FIG. 4 shows the growth tank 14 of the present invention. The growth tank is a self contained unit that fits inside the reservoir tank. The growth tank 14 comprises two opposing side walls 50 and two opposing end walls 52 together defining an open top 56. The bottom wall 58 includes two descending ramp sections 60 that converge in a rounded trough 62. A nozzle that serves as an inlet conduit 64 for the media, extends from the center of the trough 62 and is in fluid communication with the trough. The tank 14 is preferably an injection molded thermoplastic material and thereby has a slight draft to its side walls 50 and end walls 52 to enable ejection from a mold cavity. Ideally, when inserted within the reservoir tank, one side wall 50 from the cell growth tank 14, along its entire surface, will contact a side wall from the reservoir tank. The open top section 54 of the tank is skirted by a lid 16 that will fittingly engage the reservoir tank. The cell growth tank is shaped to hold a cartridge of attached plates. The outermost plates of the cartridge and the interior opposing side walls of the growth tank form additional chambers for cell growth. The spacing between the side walls and the cartridge is preferably 0.04 inches.

Figure 5A:
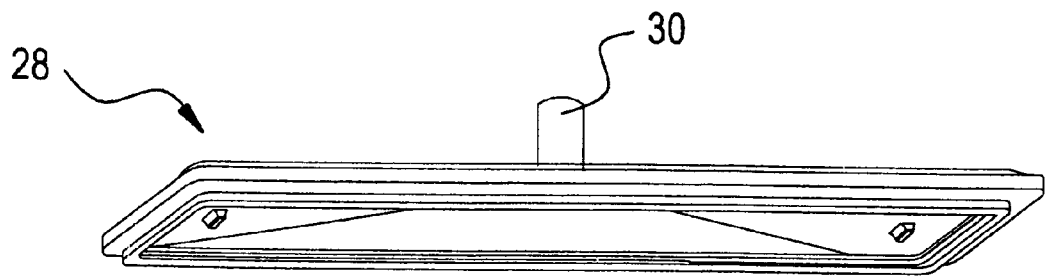
FIGS. 5A and 5B are three dimensional views of the cell growth tank lid of the present invention.
Figure 5B:
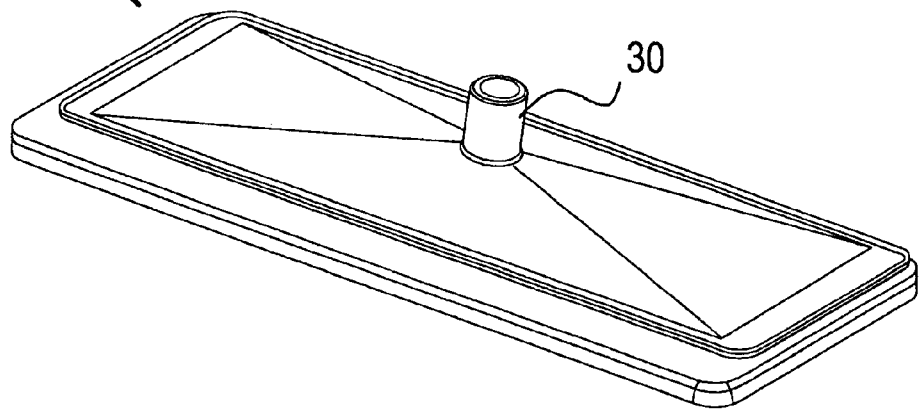

FIGS. 5A and 5B show a lid 28 that engages the open top 54 of the cell growth tank 14. The lid 28 is preferably removable so the user may remove the cartridge of plates held therein and harvest the cells that have grown on the plates. Further, the lid 28 peaks in a penthouse roof leading to a nozzle which is an outlet conduit 30 for the tank. The lid 28 takes this shape so that any air bubbles contained within the tank will ascend out through the outlet conduit and not be trapped anywhere within the tank. Further, the removable lid 28 is capable of providing an air and fluid tight seal to the cell growth chamber.

Figure 6:
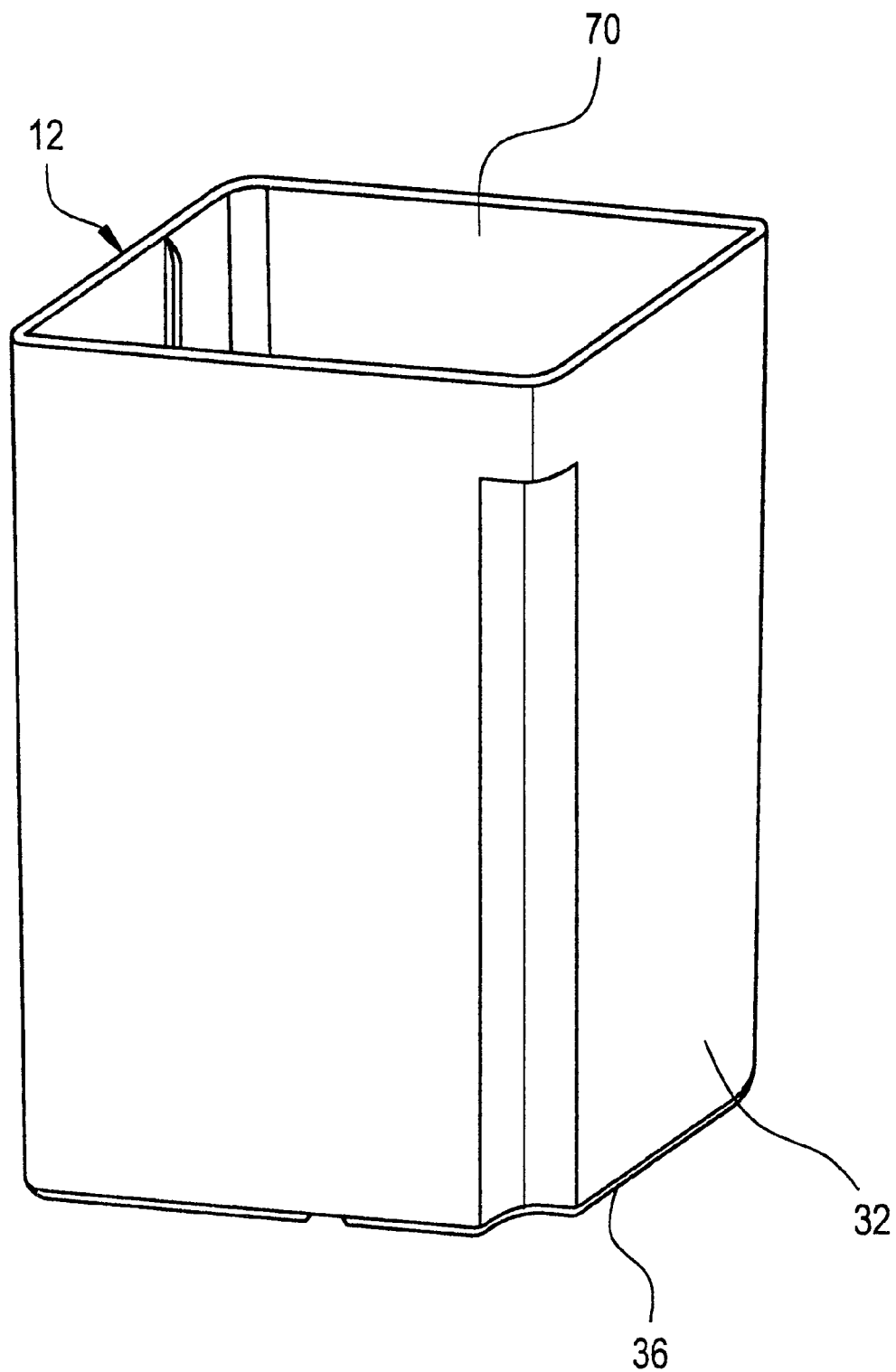
FIG. 6 is a three dimensional view of the reservoir tank of the present invention.

FIG. 6 shows the reservoir tank 12 of the present invention. The reservoir tank comprises four side walls 32 defining a bottom 36 and an open top 70. The single piece reservoir tank 12 is also preferably injection molded, and therefore preferably has a slight outward draft to its side walls 32 to enable ejection from a mold cavity. The reservoir lid/growth tank (FIG. 4) fittingly engages the reservoir tank 12 thereby forming the top of the device 34, and is preferably permanently secured together with the reservoir tank 12 along the periphery of the top of the reservoir tank by any of a variety of fabrication methods including ultrasonic welding, press fitting, gluing, solvent welding, or even gaskets.

Figure 7:
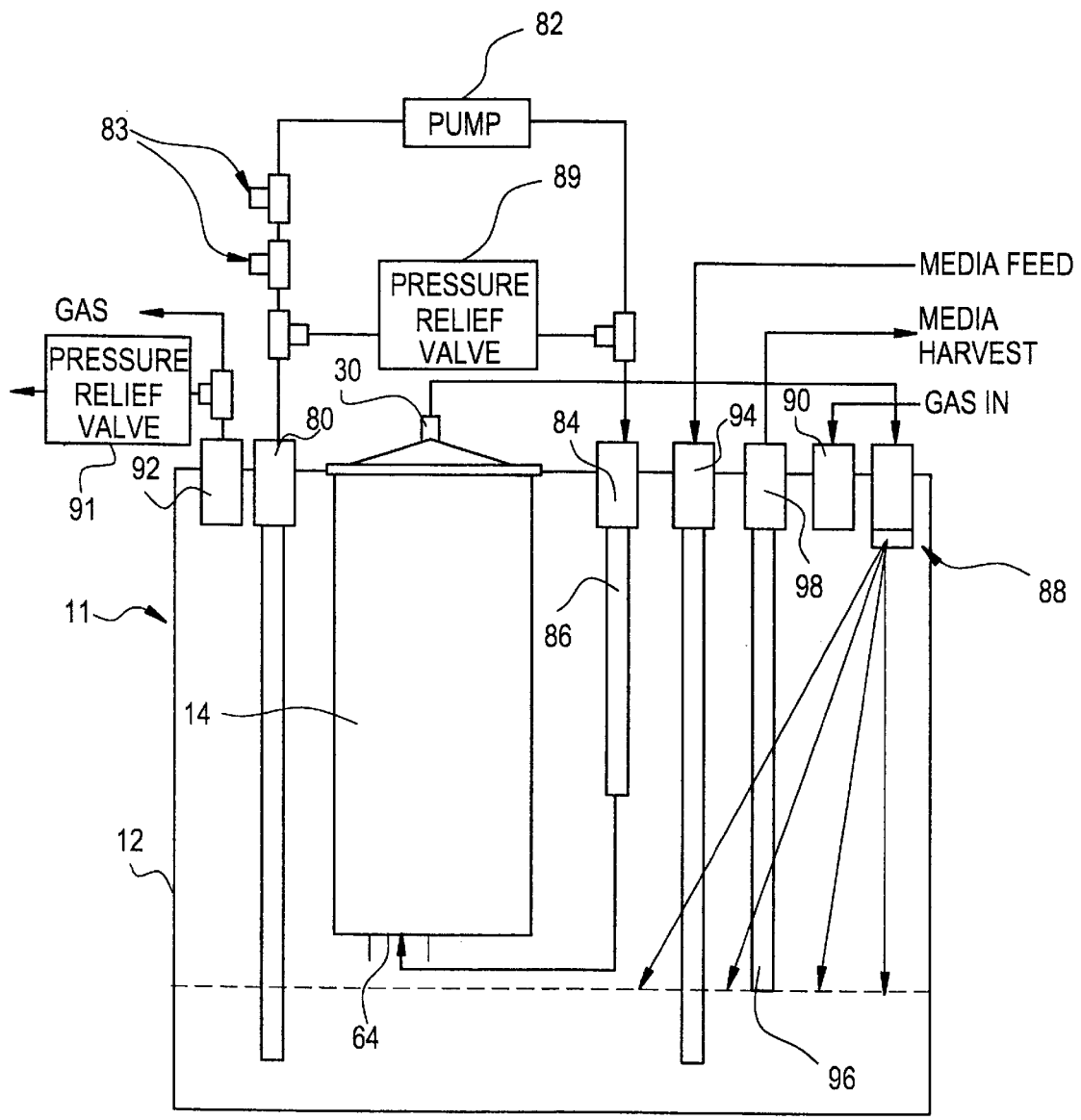
FIG. 7 is a schematic drawing illustrating the operation of the present invention.

FIG. 7 shows a schematic diagram outlining the function of the cell culture device 11 of the present invention. The cell growth tank 14 is situated within the reservoir tank 12. The reservoir tank 12 holds media, the level of which is designated by a dotted line. Lines with arrows designate connections by hose, arrow directions depict the flow pattern of the media or air within these hoses. Media is drawn from the reservoir and through an air and liquid tight fitting 80 on the reservoir tank lid by a peristaltic pump 82, which serves as a circulation pump for the device. The media drawn from the reservoir is circulated through the pump, through a liquid and air tight fitting 84 on the lid of the reservoir tank. This fitting is attached to a tube 86 that projects into the reservoir tank. The bottom of this tube 86 is fitted with a connector hose that connects with the inlet conduit 64 on the bottom wall of the cell growth tank. Media is fed along this completely sealed route into the cell growth tank 14 and flows upwardly and evenly through the growth chambers created by the stacked plates. Upon reaching the top of the tank, the media is then fed out through an outlet conduit 30. A connecting hose links the outlet conduit on the cell growth tank lid to a specialized oxygenator nozzle 88 on the lid of the reservoir tank. The now deoxygenated media is next forced back into the reservoir and preferably sprayed against a side wall of the reservoir tank, which has been treated to be hydrophilic, and allowed to run down the side wall of the tank, into the media pool below as depicted by arrows leading from the oxygenator nozzle 88. As will be discussed later, the oxygenator nozzle 88 is specially designed to spray the wall of the reservoir tank in order to prevent foaming that would result if the media were allowed to fall directly into the pool.

To replenish oxygen, which is consumed by the cell growth process, air is introduced to the system, preferably by a common aquarium pump, through a tube connected to another fitting 90 on the top of the device. The pump provides sufficient air pressure for air to breathe out of the system through another fitting 92. Thereby, when media is running along the side wall, after passing through the oxygenator nozzle 88, it will pick up the fresh oxygen that is being pumped into the system. As an alternative to atmospheric air, pure oxygen may be pumped through fitting 90 or a combination of air and oxygen. Any air or oxygen entering the system is preferably first pumped through an air filter in order to preserve the sterility of the system. It should be noted that a pump is not the only means available to introduce gases to the system. The gas may be introduced by tanks or other means. The hose running from gas outlet fitting 92 is preferably fitted with a T-fitting connected to a pressure relief valve 91 to help compensate for any pressure build-up within the system.

From an external reservoir of fresh media, a tube runs through another peristaltic pump to fitting 94. This perfusion pump very slowly introduces fresh media into the system. Spent media is drawn from the system through a sipper tube 96 and out through fitting 98 via a third pump leading to a waste container. This third pump will preferably move more media in a given time than the perfusion pump. This insures that the level of the media in the reservoir tank always remains at the level of the bottom of the sipper tube 96.

The "circulation loop", which runs from the reservoir, through fitting 80, through the circulation pump 82, through fitting 84, tube 86, and into the cell growth tank through inlet conduit 64, is preferably fitted with a series of T-fittings 83. One set of T-fittings connects the loop on either side of the pump to a pressure relief valve 89 which helps ensure that excess pressure does not build in the system. The other two fittings in the circulation loop are used to add seed media to the cell growth chamber, as will be discussed below, or can be used to extend the loop for, through a detector or analyzer, for example.

Figure 8:
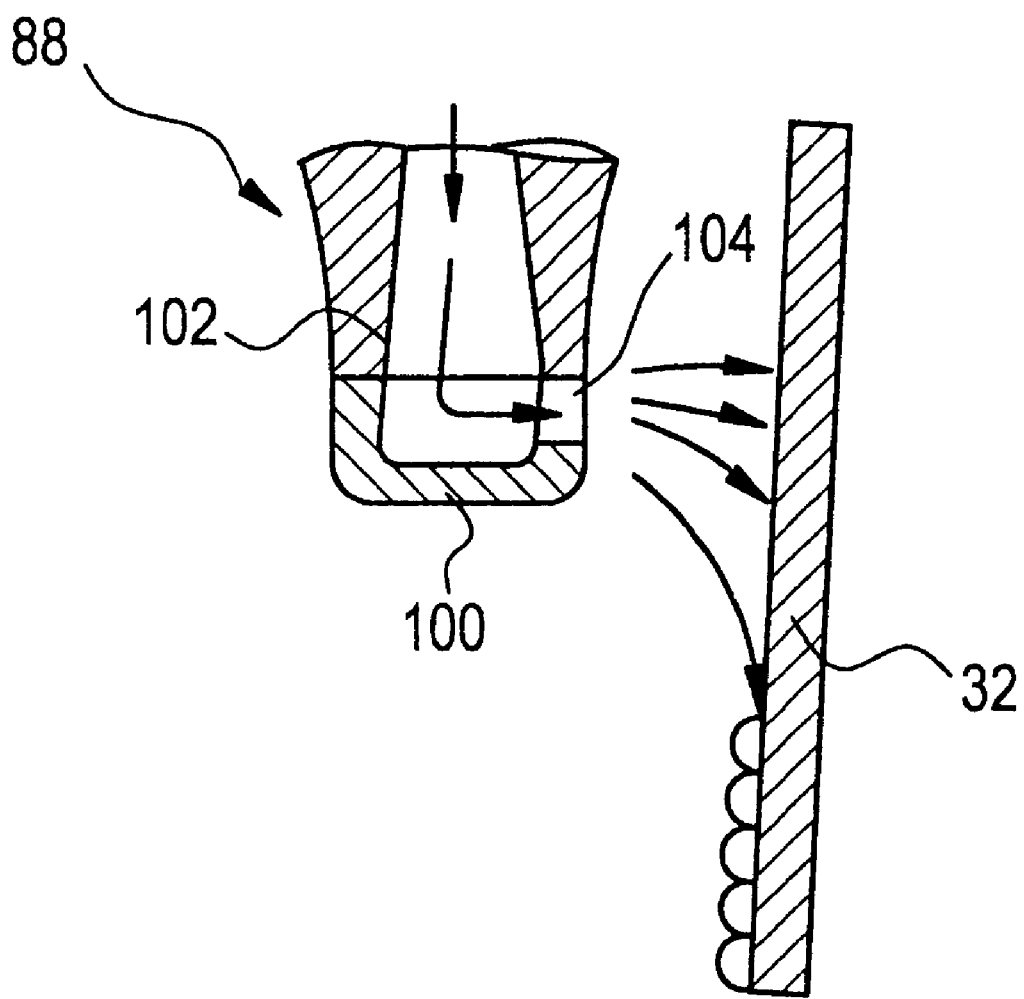
FIG. 8 is a cross-sectional view of one embodiment of an oxygenation device of the present invention.

FIG. 8 shows a preferred embodiment for a nozzle design that aids in oxygenation. As described earlier, it is important that deoxygenated media be exposed to oxygen. This is accomplished by allowing media to descend from the top the reservoir tank to the pool at the bottom. The cylindrically shaped oxygenator nozzle 88 has a solid bottom surface 100, thereby restricting downward flow. The radial side wall 102 of the nozzle has at least one aperture 104 through which a stream of media may be projected in a substantially horizontal direction. Once contacted with the side wall 32 of the reservoir tank, the liquid is held against the side wall by surface tension as it falls into the pool of media below. The side walls of the reservoir tank are preferably treated to be hydrophilic so that the media will spread out across the surface and adhere to the entire surface. An alternative to spraying the media against a side wall is to hang a screen or curtain of synthetic fabric or non-woven polyester material from the top of the reservoir tank, into the pool below, running substantially the length of the reservoir tank. The screen is also preferably hydrophilic. The media is sprayed against the screen, or alternatively allowed to fill a trough and spill over onto the screen, and held by surface tension, falls to the pool below. Foaming of the media is prevented in either case.

Figure 9:
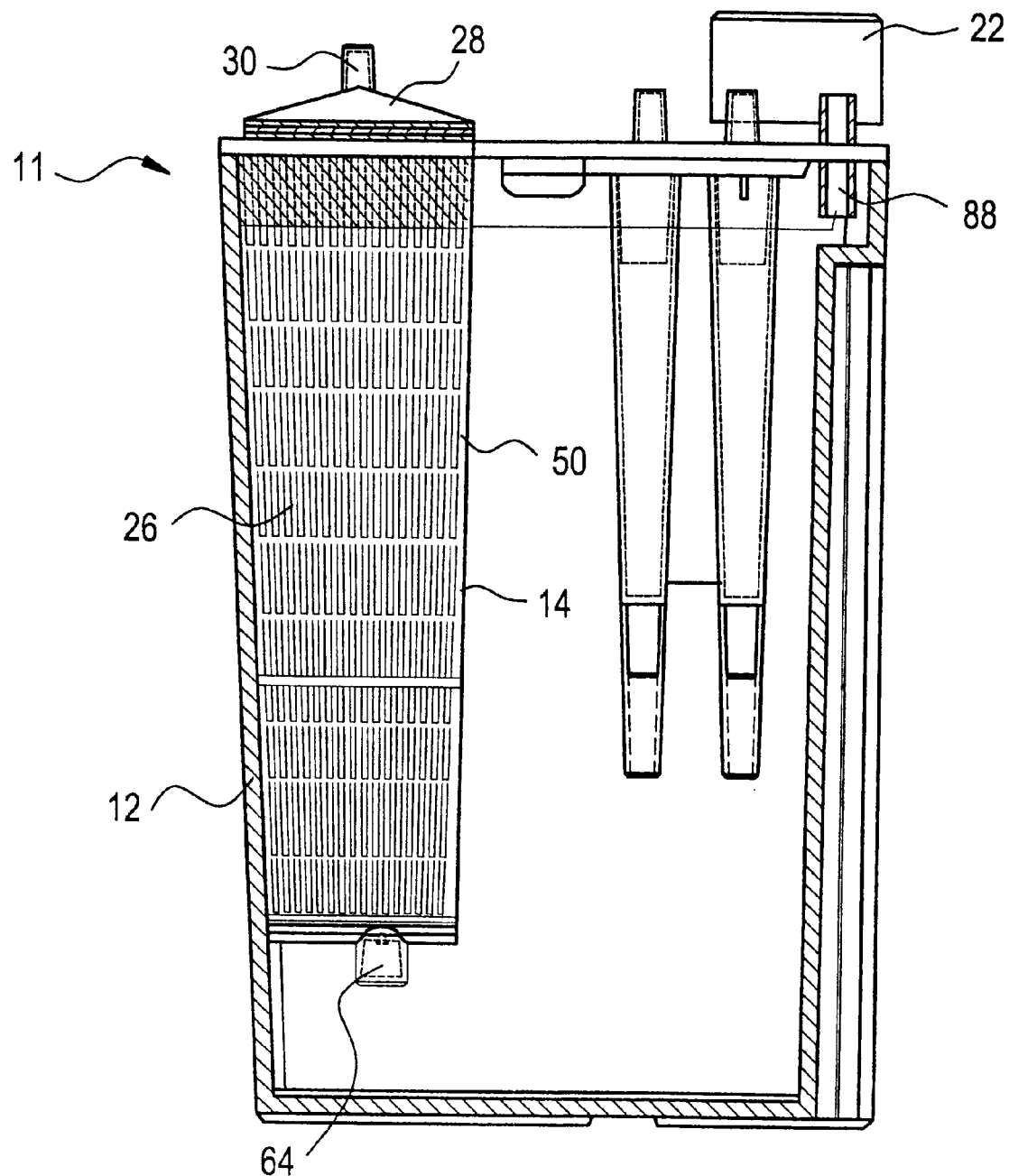
FIG. 9 is a cross-sectional view of the present invention taken along the section line A—A of FIG. 1.

FIG. 9 is a cross section of the cell culture device of the present invention taken along the section line A—A in FIG. 2. Like features from previous figures are denoted by the same numerals.

Figure 10:
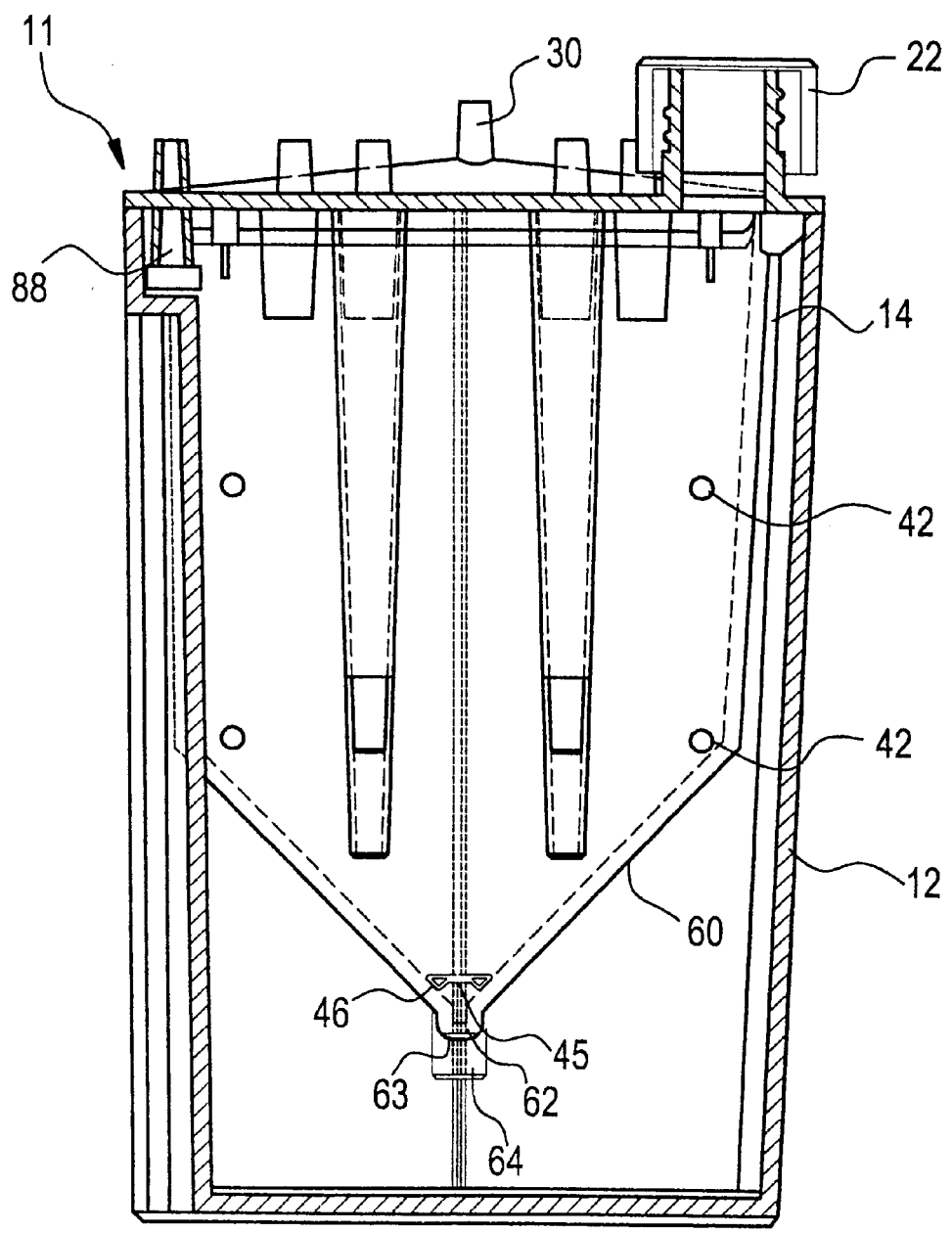
FIG. 10 is a cross-sectional view of the present invention taken along the section line B—B of FIG. 1.

FIG. 10 is a cross section of the cell culture device of the present invention taken along the section line B—B in FIG. 2. Like features from previous figures are denoted by the same numerals.

The bottom wall 60 of the cell growth tank 14 is designed to facilitate even flow into the individual chambers of the cell growth tank. The inlet conduit 64 directs flow into a trough 62 that runs perpendicular to the conduit along the bottom width of the tank. The trough 62 is defined by the radial groove formed at the bottom most part of the cell growth tank and the axial alignment of double triangular points 46 of each stacked plate. Media enters through the inlet conduit 64 and spreads laterally along the trough 62. It then is forced upwardly through the passages 45 and chambers formed by the separated and stacked plates 26. The general wedge shape of the cell growth tank 14 and plates facilitates uniform flow upwardly through the tank. The preferred intersecting or double triangular element 46 attributed to the plates helps centralize any air bubbles that enter the tank 14 and promote their exit through the restriction port, and eventually through the centralized outlet conduit nozzle 30 on the lid 28.

It is important to note that the cell growth system of the present invention is entirely self contained and can grow cells independently and without human intervention. Further, due to the closed loop nature of the system, the only sterile connections required in the system are the "media feed" fitting 94, through which fresh media enters the reservoir tank, and the two T-fittings used to seed the cell growth tank (FIG. 7). The sterility of the internal system environment cannot be threatened from outside contaminants through any other access fitting. The only other fitting that leads into the system from an outside source carries air or pure oxygen that has been forced through an air filter.

The walls of the reservoir tank, walls of the cell growth tank, and plates are preferably optically clear. The transparency provides several advantages. First, proper use and function of the device can be monitored by sight. Excess foaming can be detected, color of the media can be monitored, all internal plumbing fixtures can be observed, and cell growth can be analyzed. Second, since one side wall of the cell growth tank is preferably flush against or close to a side wall of the reservoir tank, a microscope may be used to analyze cells through the two overlapping transparent walls when the unit is laid on its side.

The position of the cell growth tank should be within the focal length of the microscope. Several steps are required for operation of the device. The first step is to attach seed cells to both sides of the 15 plates, plus the interior of the side walls 50 of the cell growth tank 14. This is accomplished by first clamping the hose that leads from the fitting 80, prior to the T-fittings, then introducing media containing the seed cells through T-fittings 83 in the circulation loop. Once the cell growth tank is filled with seed media, the hose leading from the outlet conduit 30 to the oxygenator nozzle 88 is clamped, thus isolating the growth tank from the reservoir tank 12. The device is then tipped over so that it lies with the plates in the growth tank lying in a horizontal plane. The seeds are heavier than the media and will therefore settle on one surface of the plates, and because the plates are specially treated, the cells will eventually attach to the plates such that they will stay in place when the device is returned to the vertical position.

The media is next drained from the growth tank, through a T-fitting, and the tank is flushed with fresh media. It is possible to have additional nozzles or fittings in the lid of the growth tank to help facilitate drainage of the seed media. Fresh seeded media is next introduced to the growth tank. The device is then tipped such that the plates are again horizontal, but so that opposite side of the plate now faces upward. In this manner, both sides of each plate can be seeded.

After a proper time has been allowed for the attachment of the cells, the device is turned to its upright position as shown in FIG. 2, and the seed media is again flushed out. Fresh media is introduced into the reservoir preferably through the neck on the reservoir tank lid, or alternatively through the T-fittings located within the tubing connecting the circulation pump. With attachment of the proper hoses and initiating the operation of the pumps, the device will operate indefinitely.

For the cells to grow and multiply, it is necessary for a continuous moving film of fresh media to move over them for nourishment. The media follows the circulation path as described earlier. The circulation path repeats continuously for the duration of the cell growth period, which may be as long as several weeks.

At the completion of the growth cycle, it is sometimes desirable to examine the individual plates, for example to study growth patterns using a microscope. It is also sometimes desirable to harvest the cells from the plates using a scraping tool. For these reasons, the lid to the growth tank is preferably removable.

Although the invention has been described in detail for the purpose of illustration, it is understood that such detail is solely for that purpose and variations can be made therein by those skilled in the art without departing from the spirit and scope of the invention which is defined by the following claims.

We claim:

1. A tissue culture device comprising:
   a reservoir tank capable of containing fluid;
   a cell growth tank situated within said reservoir tank having a plurality of cell growth chambers, the interior surfaces of said growth chambers adapted for the growth of cells;
   an inlet conduit for providing a source of fluid to the chambers;
   an outlet conduit adapted to be in fluid communication with fluid in said reservoir tank; and
   a circulation pump connecting said inlet conduit to said fluid in said reservoir tank.

2. A tissue culture device as claimed in claim 1 wherein the cell growth chambers are defined by the spacings between a plurality of stacked plates.

3. A tissue culture device as claimed in claim 1 further comprising an inlet through which fluid from an external source may be pumped into said reservoir tank.

4. The tissue culture device of claim 3 further comprising a sipper tube extending into said reservoir tank to a predetermined depth, said sipper tube connected to an external pump capable of drawing fluid from said reservoir.

5. The tissue culture device of claim 4 further comprising at least one air inlet in said reservoir tank capable of attachment to a pump through which said pump delivers air into said reservoir tank; and at least one air outlet in said reservoir tank capable of venting air from within said reservoir tank, whereby an air flow is created between said air inlet and said air outlet by differential pressure.

6. The tissue culture device of claim 5 further comprising a media spreading oxygenator nozzle having cylindrical side walls having at least one aperture therein, a solid bottom, and an open top, said nozzle extending into said reservoir tank, whereby said outlet conduit is fluidly attached to said top of said oxygenator nozzle.

7. The tissue culture device of claim 6 further comprising a curtain suspended within said reservoir tank and substantially extending the length of the tank.

8. The tissue culture device of claim 1 wherein a removable lid forms a top surface of said cell growth tank.

9. The tissue culture device of claim 1 wherein said reservoir tank and said cell growth tank are formed of a transparent material.

10. The tissue culture device of claim 1 further comprising passages for providing fluid communication between said inlet conduit and each of said growth chambers.

11. The tissue culture device of claim 1 wherein said inlet conduit is fluidly attached to a trough running longitudinally along a bottom wall of said cell growth tank.

12. The tissue culture device of claim 1 wherein said reservoir tank and said cell growth tank are optically clear.

* * * * *